(12) United States Patent
Ostrovsky

(10) Patent No.: US 9,265,586 B2
(45) Date of Patent: Feb. 23, 2016

(54) DEVICE AND METHOD FOR SHIELDING THE URETHRA AND BLADDER

(75) Inventor: Isaac Ostrovsky, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2334 days.

(21) Appl. No.: 11/284,746

(22) Filed: Nov. 22, 2005

(65) Prior Publication Data

US 2007/0113858 A1    May 24, 2007

(51) Int. Cl.
 *A61F 13/00* (2006.01)
 *A61B 19/00* (2006.01)
(52) U.S. Cl.
 CPC ......... *A61B 19/40* (2013.01); *A61B 2019/4036* (2013.01)
(58) Field of Classification Search
 CPC ........... A61B 2019/4036; A61B 19/40; A61N 5/061; A61N 5/0611
 USPC ...................... 606/13–15, 17, 27; 607/33, 99, 607/101–102; 600/11, 114, 117, 121, 135
 See application file for complete search history.

(56) References Cited

U.S. PATENT DOCUMENTS

| | | | |
|---|---|---|---|
| 5,468,239 | A | 11/1995 | Tanner et al. |
| 2003/0083654 | A1 | 5/2003 | Chin et al. |

FOREIGN PATENT DOCUMENTS

| | | |
|---|---|---|
| EP | 1 170 034 | 1/2002 |
| WO | 00/24463 | 5/2000 |

*Primary Examiner* — Nicholas Woodall
*Assistant Examiner* — Camtu Nguyen

(57) ABSTRACT

A device for managing heating energy from a probe comprises a sleeve including a lumen sized to receive the probe therein, the sleeve defining a first window which, when the sleeve is in a desired position, faces target tissue to which the probe is to deliver energy and a shield element protecting non-target tissue from energy emanating from the surgical probe, the shield element being formed of one of a material reflecting energy delivered by the probe and a material absorbing energy delivered by the probe in combination with a positioning element which, when the sleeve is in the desired position, contacts an anatomical structure to position the sleeve relative to the target tissue.

15 Claims, 5 Drawing Sheets

DEVICE AND METHOD FOR SHIELDING THE URETHRA AND BLADDER

BACKGROUND

Many medical conditions are treated by applying heat to necrose or shrink tissue. A surgical probe is generally used to apply heating energy to the target tissue. However, in many cases energy is also applied to non-targeted tissue. This energy is not only wasted, it may also damage tissue while providing no therapeutic benefit.

SUMMARY OF THE INVENTION

The present invention is directed to a device for managing heating energy from a probe, the device comprising a sleeve including a lumen sized to receive the probe therein, the sleeve defining a first window which, when the sleeve is in a desired position, faces target tissue to which the probe is to deliver energy and a shield element protecting non-target tissue from energy emanating from the surgical probe, the shield element being formed of one of a material reflecting energy delivered by the probe and a material absorbing energy delivered by the probe in combination with a positioning element which, when the sleeve is in the desired position, contacts an anatomical structure to position the sleeve relative to the target tissue.

DETAILED DESCRIPTION

Figure 1:
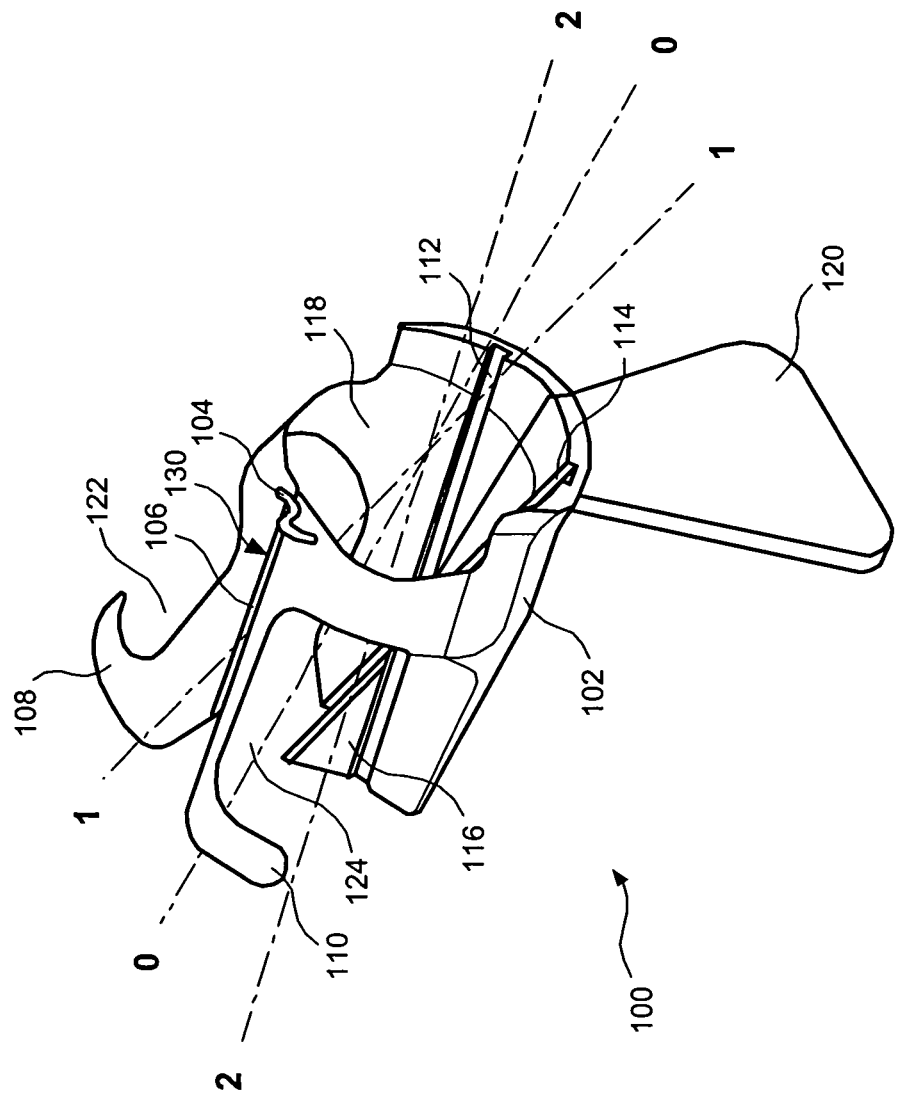
FIG. 1 shows a perspective view of an embodiment of a shielding device according to the present invention.
Figure 2:
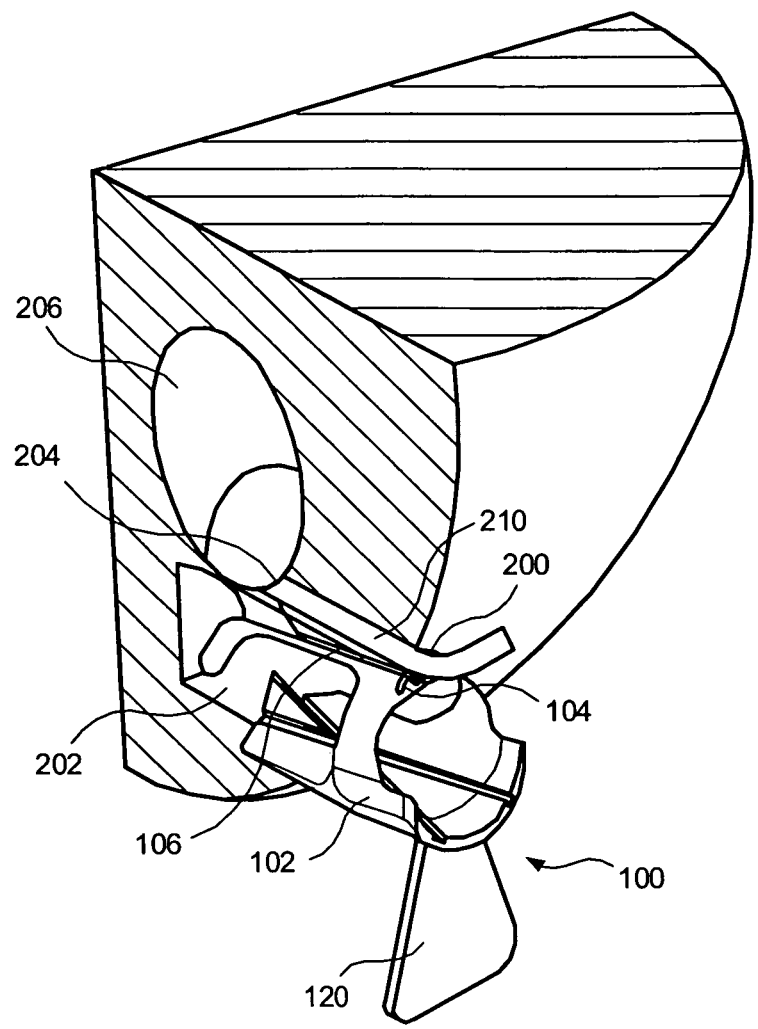
FIG. 2 shows a perspective view of the shielding device shown in FIG. 1 positioned in a schematic representation of a vaginal canal, according to the present invention.
Figure 3:
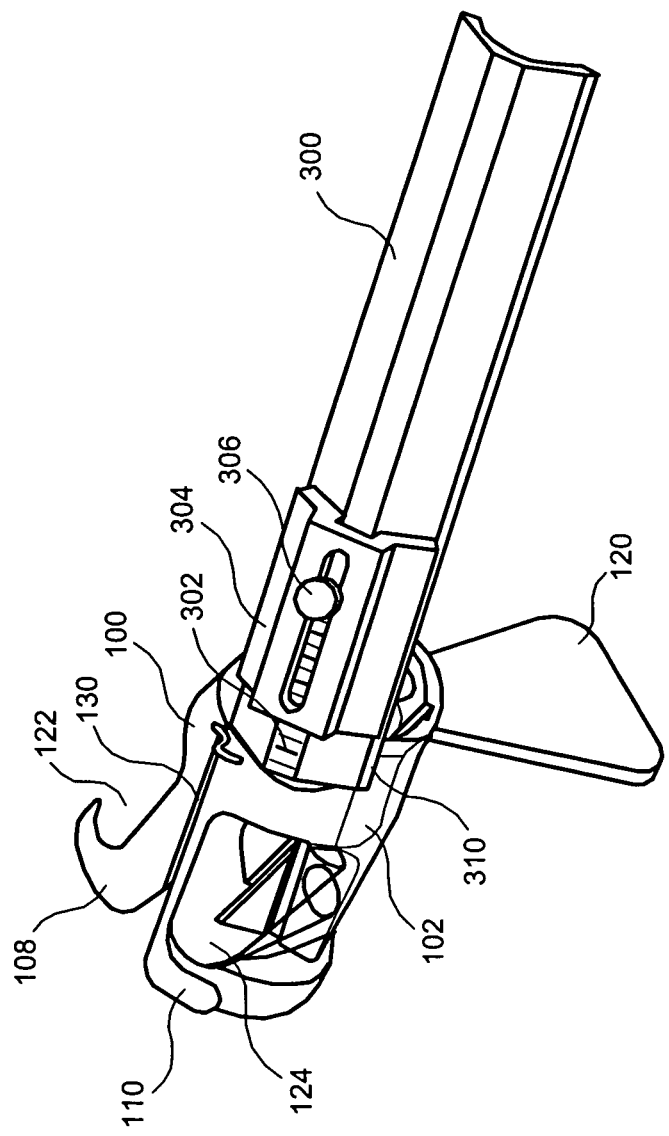
FIG. 3 shows a perspective view of the shielding device shown in FIG. 1 with a heating probe inserted therein, according to the present invention.
Figure 4:
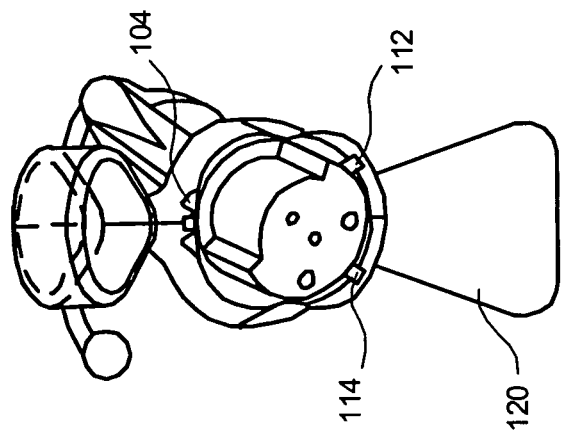
FIG. 4 shows a perspective view of the shielding device shown in FIG. 1 according to a first lesion formation.

The present invention may be further understood with reference to the following description and the appended drawings, wherein like elements are referred to with the same reference numerals. The invention relates to devices for shielding non-targeted tissue from heat applied to adjacent target tissue. In particular, the present invention relates to a system for shielding portions of the urethra and bladder during heat treatment of the endopelvic fascia to reduce the symptoms of stress urinary incontinence.

As described above, certain medical conditions are treated by heating target tissue to achieve a therapeutic result (e.g., to denature collagen and shrink the tissue). Stress Urinary Incontinence (SUI) is often treated in this way by heating a portion of the endopelvic fascia near the bladder, to improve continence by repositioning the bladder or bladder neck.

In order to improve the efficiency of tissue heating procedures and to minimize damage to non-targeted tissue, it is important to minimize the transmission of heat to non-targeted tissue. Properly positioning the device to aim heating energy as well as possible toward the target tissue is an important step in achieving this goal. The present invention provides a device for assisting the user in properly positioning a heat delivery device while shielding non-targeted tissue from the heating energy.

Exemplary embodiments of the present invention describe a device and method for protecting non-targeted tissue from heating during employment of an energy source (e.g., an ultrasound probe) inserted within a body lumen or hollow organ. More specifically, embodiments of the invention provide a shield which protects the urethra and bladder by permitting energy to be transmitted out of the shield only through openings which, when the shield in a desired position, are directed toward areas of target tissue. Energy directed toward other areas is prevented from leaving the shield. Thus, when an energy delivery probe is properly inserted within the shield inside the vaginal canal, only energy delivered therefrom toward openings in the shield passes to he tissue while, when improperly positioned therein out of alignment with openings in the shield, a large portion of the energy directed therefrom is prevented from leaving the shield and prevented from heating tissue. Embodiments of the invention may also be used to guide the heating probe toward a proper orientation and to limit its advancement within the vaginal canal to a desired depth.

As described above, devices delivering various types of energy have been employed in heat treatment of tissue including, for example, radio frequency (RF) energy, high intensity ultrasound, microwaves, and optical laser energy. Furthermore, certain techniques employing these energy types comprise invasive procedures, in which an incision is made to insert an energy delivery element into or adjacent to the target tissue. In other techniques, energy delivery devices remain outside the body or are inserted into body lumens via naturally occurring body orifices. Energy is delivered by these devices to internal target tissue through the intervening tissue (i.e., through the skin or lumenal wall and intervening tissue). For example, techniques utilizing high intensity ultrasound or optical energy are often non-invasive or minimally invasive.

As will be described in more detail below, a guiding device according to the invention includes a tubular sleeve inserted into a body lumen via a naturally occurring body orifice to a desired depth relative to a target portion of tissue to be heated. This target position may be indicated, for example, by a positioning member engaging an anatomical feature adjacent to the orifice. A heating element is then inserted into the sleeve to a target position relative to the target tissue. The sleeve preferably includes guiding elements to guide the heating element toward the target position and a stop element to prevent the sleeve from being inserted beyond a desired treatment position. Thus, the sleeve assists the user of the heating device in properly positioning the device and in maintaining the device in this position during the procedure. As described above, the sleeve also preferably comprises one or more protective elements shielding non-targeted portions of tissue from heating energy emanating from the device. For example, energy may be directed by the device toward non-targeted tissue as energy radiates therefrom in directions other than a target direction and/or when the device is improperly positioned within the lumen.

The following description of the guiding/positioning and protective device and method according to the invention refers to a vaginally insertable ultrasound probe used to heat the endopelvic fascia to treat SUI. However, those skilled in the art will understand that this invention may be used in any number of invasive and non-invasive procedures in conjunction with a variety of energy sources.

During procedures to treat SUI, the energy source is aimed at a target portion of the endopelvic fascia attached to the urethra and the anterior vaginal wall. As the heated fascia shrinks, it tightens around the urethra and stabilizes to reposition the bladder and improve continence. Depending on the severity of the condition, among other factors, a user may decide to use RF current or high intensity ultrasound probe to heat the endopelvic fascia. Regardless of the energy type selected, conventional heating probes for SUI therapies, generally provide no protection or shielding for non-targeted tissues near the targeted tissue. The lack of protection as well as difficulties in accurately positioning and aiming these devices may result in less than optimal performance and may adversely affect non-targeted tissues. Difficulties in properly positioning these devices result, at least partly, from the fact that reference measurements used to locate these devices are generally dependant on relations between anatomical features which may vary significantly from patient to patient.

As shown in FIG. 1-6, an exemplary guiding/positioning and protective system according to an embodiment of the present invention includes a sleeve 100 which facilitates the guiding and positioning of an ultrasound heating probe 300 (FIG. 3) and which protects non-targeted portions of the urethra and bladder from the energy transmitted by the probe. The sleeve 100 comprises a substantially tubular body 102 defining a passage 118 therethrough. Those skilled in the art will understand that the term "tubular" in this context encompasses a range of cross-sectional shapes selected to fit the anatomy of the passage or passages into which the sleeve 100 is to be inserted (in this case the vaginal canal) and that the cross-sectional shape and area of this sleeve 100 may vary along its length. The passage 118 is sized to enable the heating probe 300 to be advanced therethrough to a desired position within the sleeve 100. The tubular body 102 comprises guide elements (in this embodiment, a pair of probe guiding grooved channels 112, 114) which guide the probe 300 toward a proper location and orientation from which to deliver energy to the target tissue.

Figure 6:
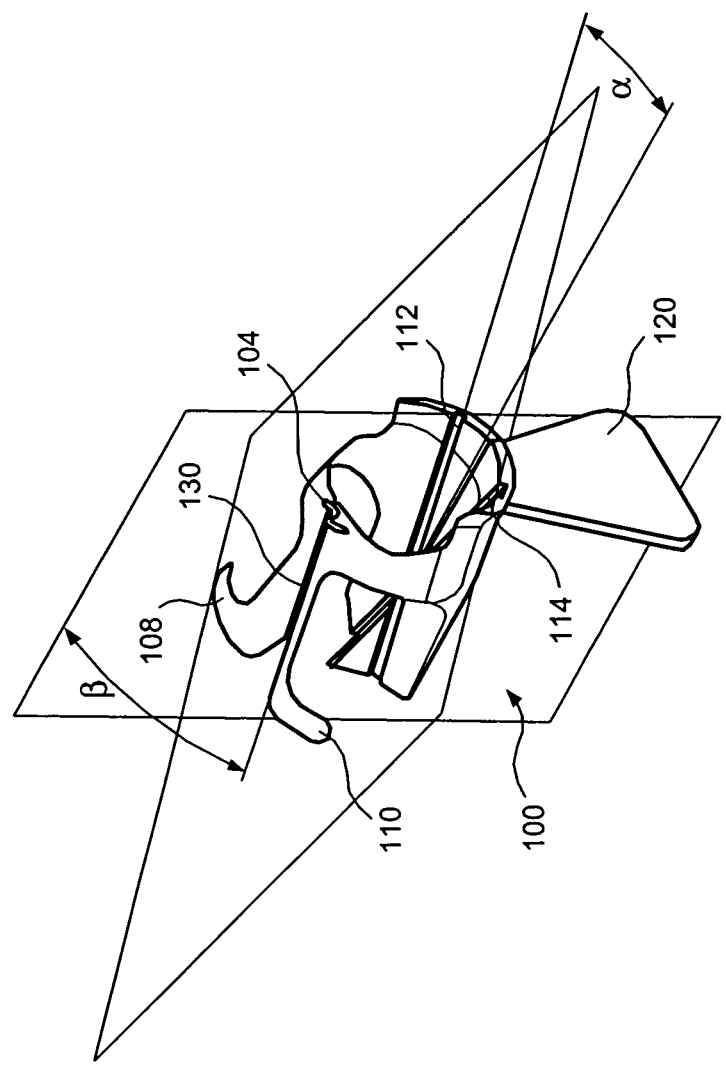
FIG. 6 shows a perspective view of the shielding device shown in FIG. 1 positioned at a first angle with respect to the longitudinal axis of the sleeve and a second angle with respect to the vertical axis of the sleeve.

The sleeve 100 includes a positioning mount 104 which when coupled to a positioning mechanism, as described in detail below, enables a user to insert the sleeve into the vagina to a desired depth relative to a target portion of the urethra. In addition, the passage 118 assists in angularly aligning the probe 300 relative to an axis of the vaginal canal so that it faces the target portion of the endopelvic fascia. For example, the positioning mount 104 indicates an angular orientation of the sleeve 100 within the vaginal canal and the grooved channels 112 and 114 which receive a key or other protrusion (not shown) of the probe 300 to maintain the probe 300 in a desired orientation with respect to the sleeve 100. More specifically, the grooves 112, 114 according to this embodiment extend on an inner surface of the tubular body 102 along axes 1-1 and 2-2. The grooves 112, 114 may, for example, be substantially symmetric with respect to a longitudinal axis 0-0 of the tubular body 102 which is substantially parallel to a longitudinal axis of the vaginal canal when inserted therein so that the sleeve 100 provides two locations for and energy delivery head of the probe 300 on either side of the axis of the vaginal canal and spaced therefrom by a substantially equal distance. The offset of the probe 300 from the axis of the vagina also helps to prevent energy transmitted by the probe 300 from being directed into the bladder and urethra. In one exemplary embodiment, the first angle (α) between the channel axes 1-1, 2-2 and the longitudinal axis 0-0 is approximately 15 degrees (FIG. 6). That is, an angle formed between each of the axes 1-1 and 2-2 and the axis 0-0 on a distal side of an intersection of these axes is approximately 15°. The angle may range from 10 to 20 degrees depending on the beam diameter and the size of the patient.

Figure 5:
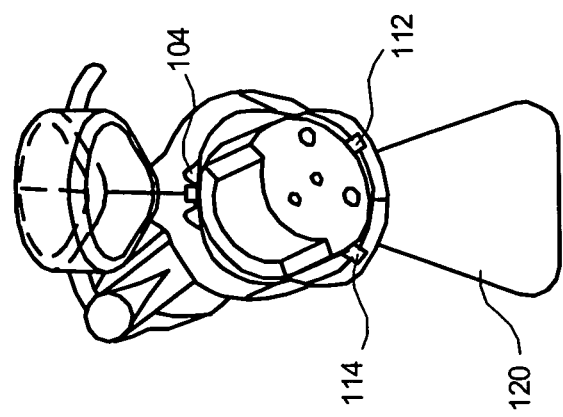
FIG. 5 shows a perspective view of the shielding device shown in FIG. 1 according to a second lesion formation.

The grooves 112, 114 are also angled with respect to a plane including the vertical axis of the sleeve 100 so that an angular orientation of the probe 300 within the sleeve 100 is limited to 2 formations, one with respect to the axis of the sleeve when in the right groove (FIG. 4), and an opposite symmetric orientation when in the left groove (FIG. 5). The grooved channels 112, 114 cooperate with guided elements such as keys or other protrusions of the probe 300, so that the probe 300 can be inserted into the sleeve 100 along each of the grooved channels 112, 114 in only one angular orientation. This orientation is offset by a second angle from a vertical axis of the sleeve 100 to minimize an amount of energy reaching the urethra from the probe 300. In this embodiment, the angle is approximately 35°. The angle may range from 20 to 45 degrees depending on the energy beam diameter and the size of the patient.

An optional ramp element 116 may also be included in the sleeve 100 to further guide the probe 300, by offsetting the distal end of the probe 300 toward a portion of the inner surface of the tubular body 102 which, when in the desired position, contacts the wall of the vagina adjacent to the target tissue. This reduces the likelihood that a gap will be formed between the probe and the tissue through which the energy will need to be transmitted and minimizes the size of any gap so formed.

For example, the grooved channels 112, 114 and the keys of the probe 300 prevent rotation of the probe 300 within the passage 118 of the sleeve 100, so that the probe 300 remains in the correct angular orientation to avoid injuries to the urethra. In one exemplary embodiment, as shown in FIG. 6, the angle of insertion of the probe 300 into the sleeve 100, the second angle (β) is about 35 degrees from a vertical axis of the sleeve 100. Since two grooved channels are provided, the probe 300 may be inserted in two orientations, to treat two portions of the endopelvic fascia that are symmetrical about the urethra.

As described above, the sleeve 100 comprises a positioning mount 104 which sets the depth to which the sleeve 100 will be inserted into the vagina. Those skilled in the art will understand that the depth of the insertion of the sleeve 100 in the vagina refers to the depth of a portion of the sleeve 100 at which an energy delivery head of the probe 300 will be located (e.g., the probe head location) when in a desired position within the sleeve 100. Before the sleeve is inserted, the length of the urethra is measured as is known in the art (e.g., using a Foley catheter) to determine a depth along the urethra of a target portion of the endopelvic fascia to be shrunk. In many cases this depth is selected to be approximately half of the length of the urethra. Those skilled in the art will understand that, although the urethra and the vagina extend generally parallel to one another, the urethral meatus and the vaginal opening are offset from one another by a distance which varies from person to person. Thus, inserting a device into the vagina by the depth measured within the urethra will position the device adjacent to a different portion of tissue than that adjacent to the target portion of the urethra. Thus, by extending a stop member laterally to the urethral meatus, the present invention ensures that the depth to which the sleeve 100 is inserted into the vagina is appropriate to place the probe head location adjacent to the target tissue. The sleeve 100 may also be constructed in multiple sizes, to match the anatomies of different patients.

Specifically, the positioning mount 104 receives a movable sliding stop 304 which may be locked in place by a locking mechanism (e.g., a lock screw 306). The sliding stop 304 is then positioned so that a distance between the stop 304 and the probe head location is substantially equal to the target tissue depth within the urethra. The lock screw 304 is adjusted to lock the stop 304 in this position and the sleeve 100 is inserted into the vagina until the stop 304 abuts the urethral meatus. The stop 304 preferably extends away from the axis of the sleeve 100 so that a depth of the probe head location is substantially equal to a depth of the target portion of the endopelvic fascia. Of course, those skilled in the art will understand that any number of geometric relationships are possible between the end of the stop 304 which abuts the urethral meatus and the end of the stop 304 which couples to the sleeve 100. So long as this relationship is known, the correlation between a selected depth within the urethra and a depth within the vagina will be known. A longitudinal position ruler 302 may be provided adjacent to the sliding stop 304, to give a representation of the extension of the probe 300 beyond the sliding stop 304. This distance may be correlated to the reference distance measured from the length of the patient's urethra 204, as described above. Furthermore, a groove 106 formed on a portion of the sleeve 100 which faces the urethral meatus when the sleeve 100 is inserted in the vagina may be designed to accept a Foley catheter 210 therethrough into the urethra 204. A handle 120 may also be provided on the sleeve 100 to more easily manipulate and put in place the device.

While the exemplary sleeve 100 simplifies the correct positioning of the heating probe 300, a user may still incorrectly position the heating probe 300. The sleeve 100 thus comprises features designed to shield nearby non-targeted tissue from inadvertent irradiation. For example, the bladder 206 and the urethra 204 are the closest vital organs to the endopelvic fascia, and are protected as described below from heating by elements of the sleeve 100.

In one exemplary embodiment, the sleeve 100 comprises a pair of thin wings 108, 110 that act as left and right bladder protectors. A urethra protector 130 is also provided along the longitudinal axis of the sleeve 100. As described above, the exemplary embodiment of the heating probe 300 uses ultrasound energy to heat target tissue. Thus the material of the thin wings 108, 110 and of the urethra protector 130 is designed to absorb or deflect the acoustic energy of the probe 300 back toward the probe 300. For example, the material may be selected so that there is a mismatch in acoustic impedance between the sleeve 100 and the surrounding tissue, so that the acoustic energy is reflected back from the interface between the tissue and the shielding material. Exemplary materials suitable for the sleeve 100 comprise metals such as stainless steel, ceramics and plastics such as polycarbonate.

As described above, the sleeve 100 comprises two grooves 112, 114 to guide the advancement of the probe 300 in two separate angular orientations. Accordingly, the ultrasound probe 300 may be inserted into the sleeve 100 along the groove 112 to irradiate target tissue from a first angle through a first one of the windows 122 of the sleeve 100 and then, after this tissue has been treated, the probe 300 is inserted into the sleeve 100 along the groove 114 to heat target tissue from a second angle through the second window 124. As described above, when the stop 304 has been positioned as described above and the sleeve 100 is inserted into the vagina until the stop 304 contacts the urethral meatus, the windows 122, 124 are aimed at the target portions of the endopelvic fascia.

Thus, when the probe 300 is inserted into the sleeve 100, the ultrasound energy is directed through the windows 122, 124 to irradiate the target portions of the endopelvic fascia while energy directed toward other tissue is absorbed or redirected inward by the sleeve 100. Furthermore, a user who incorrectly placed the probe 300 inside the vagina 202, the ultrasound energy would miss the windows 122, 124 to be reflected back or absorbed by the bladder protecting wings 108, 110 and by the urethra protector 130. The non-targeted tissue thus would not be harmed by inadvertent exposure to the heating energy.

The present invention has been described with reference to specific exemplary embodiments. Those skilled in the art will understand that changes may be made in details, particularly in matters of shape, size, material and arrangement of parts. Accordingly, various modifications and changes may be made to the embodiments described herein. The specifications and drawings are, therefore, to be regarded in an illustrative rather than a restrictive sense.

What is claimed is:

1. A device for managing heating energy from a probe, the device comprising:
    a sleeve sized and shaped for insertion into a vagina including a lumen sized to receive the probe therein, the sleeve defining a first window which, when the sleeve is in a desired position, faces target tissue to which the probe is to deliver energy;
    a shield element coupled to the sleeve and positioned, when the sleeve is in the desired position, to block a portion of the energy emitted from the probe to protect non-target tissue while permitting energy emanating from the surgical probe to pass to the target tissue, the shield element being formed of one of a material reflecting energy delivered by the probe and a material absorbing energy delivered by the probe, the shield element having a first protective element positioned to block energy emitted from the probe along a path extending to a urethra and a second protective element positioned to block energy emitted from the probe along a path extending to a bladder, the second protective element extending at an angle with respect to a longitudinal axis of the sleeve and with respect to the first protective element; and
    a positioning element coupled to the sleeve which, when the sleeve is in the desired position, contacts an anatomical structure to limit a depth of insertion of the sleeve to position the first window at a depth corresponding to the target tissue.

2. The device according to claim 1, further comprising a handle coupled to the sleeve.

3. The device according to claim 2, further comprising a first groove formed within the lumen for receiving the positioning element of the probe to guide the probe to a first target position within the lumen.

4. The device according to claim 3, wherein the first angle is about 15 degrees.

5. The device according to claim 3, wherein the first groove extends at a first angle with respect to the longitudinal axis of the sleeve, such that the probe extends at a desired orientation within the vagina.

6. The device according to claim 3, wherein the sleeve includes a ramp at a second angle with respect to a vertical axis of the sleeve, such that the positioning element of the probe is received by the first groove.

7. The device according to claim 6, wherein the second angle is about 35 degrees.

8. The device according to claim 2, further comprising a guide element projecting into the lumen to urge an energy delivering head of the probe toward a portion of a wall of the vagina adjacent to the target tissue.

9. The device according to claim 2, wherein the probe is an ultrasound probe and wherein the shield element is formed of a material selected to have an acoustic impedance mismatched with respect to an acoustic impedance of tissue of a wall of the vagina so that ultrasound energy from the probe is reflected back from an interface between the shield element and the wall of the vagina.

10. The device according to claim 1, wherein, when inserted into the vagina to the desired position, the positioning element contacts tissue adjacent to a second body orifice.

11. The device according to claim 3, further comprising a second groove formed within the lumen, the first and second grooves being disposed on either side of the axis of the sleeve substantially symmetrically.

12. The device according to claim 11, wherein the positioning element of the probe is received by the second groove, such that an angle orientation is opposite and symmetrical to that of the positioning element in the first groove.

13. The device according to claim 1, wherein the sleeve is formed of one of stainless steel, ceramic and polycarbonate.

14. The device according to claim 1, wherein the positioning element is movably coupled to the sleeve to adjust a distance between the positioning element and the first window.

15. The device according to claim 1, further comprising a probe stop limiting advancement of the probe through the sleeve.

* * * * *